(12) United States Patent
Yang et al.

(10) Patent No.: US 7,491,365 B2
(45) Date of Patent: Feb. 17, 2009

(54) RETRACTING MECHANISM FOR A BIO READER

(75) Inventors: Lu-Hung Yang, Taichung Hsien (TW); Tzer-Ming Chen, Taipei (TW)

(73) Assignee: Eumed Biotechnology Co., Ltd., Taipei Hsien (TW)

( * ) Notice: Subject to any disclaimer, the term of this patent is extended or adjusted under 35 U.S.C. 154(b) by 474 days.

(21) Appl. No.: 11/223,109

(22) Filed: Sep. 12, 2005

(65) Prior Publication Data

US 2007/0059958 A1 Mar. 15, 2007

(51) Int. Cl.
*G01N 15/06* (2006.01)
(52) U.S. Cl. .................................. 422/68.1
(58) Field of Classification Search ............... 422/102, 422/68.1
See application file for complete search history.

(56) References Cited

FOREIGN PATENT DOCUMENTS

| EP | 1321769 | 6/2003 |
|----|---------|--------|
| EP | 1352611 | 10/2003 |
| EP | 1480037 | 11/2004 |
| WO | WO2004/063747 | 7/2004 |

*Primary Examiner*—Walter D Griffin
*Assistant Examiner*—Bobby Ramdhanie
(74) *Attorney, Agent, or Firm*—Rosenberg, Klein & Lee

(57) ABSTRACT

A bio reader includes a casing defined therein a receiving space to receive therein a circuit board, a monitor electrically connected to the circuit board and a strip connector electrically connected to the circuit board for receiving therein a strip. The strip connector has a base mounted in the casing, a push movably connected to the base and having a ridge formed thereon for abutment of a strip on top of the push and an extension extending into the base and a retracting finger securely connected to the push and adapted to be slidably mounted on a side of the casing such that movement of the retracting finger is able to drive the push to move such that the strip on top of the push is also moved.

9 Claims, 5 Drawing Sheets

RETRACTING MECHANISM FOR A BIO READER

BACKGROUND OF THE INVENTION

1. Field of the Invention

The present invention relates to a retracting mechanism, and more particularly to a retracting mechanism for a bio reader able to read information of a strip inserted into the bio reader.

2. Description of Related Art

When taking a test with regard to physical conditions of a patient, a medical specialist manually transports a strip into a bio reader so that the bio reader is able to analyze the bio features contained on the strip so as to determine the physical conditions of the patient. While transporting the strip, inevitably, the medical specialist may contaminate the bio sample on the strip or the medical specialist may be infected by the bio sample. That is, medical specialists are constantly exposed to the threat of infection and the bio sample is also under the threat of being contaminated.

To overcome the shortcomings, the present invention tends to provide an improved retracting mechanism for a bio reader to mitigate the aforementioned problems.

SUMMARY OF THE INVENTION

The primary objective of the present invention is to provide an improved retracting mechanism a slidable button mounted on a side of the reader and having a linkage securely connected to a slider such that when the slidable button is moved, the slider is moved and the strip received inside the bio reader is retracted.

In one aspect of the present invention, the retracting mechanism further has a recoil spring to allow the slidable button to return to its original position after the slidable button is moved.

Other objects, advantages and novel features of the invention will become more apparent from the following detailed description when taken in conjunction with the accompanying drawings.

DETAILED DESCRIPTION OF THE PREFERRED EMBODIMENT

Figure 1:
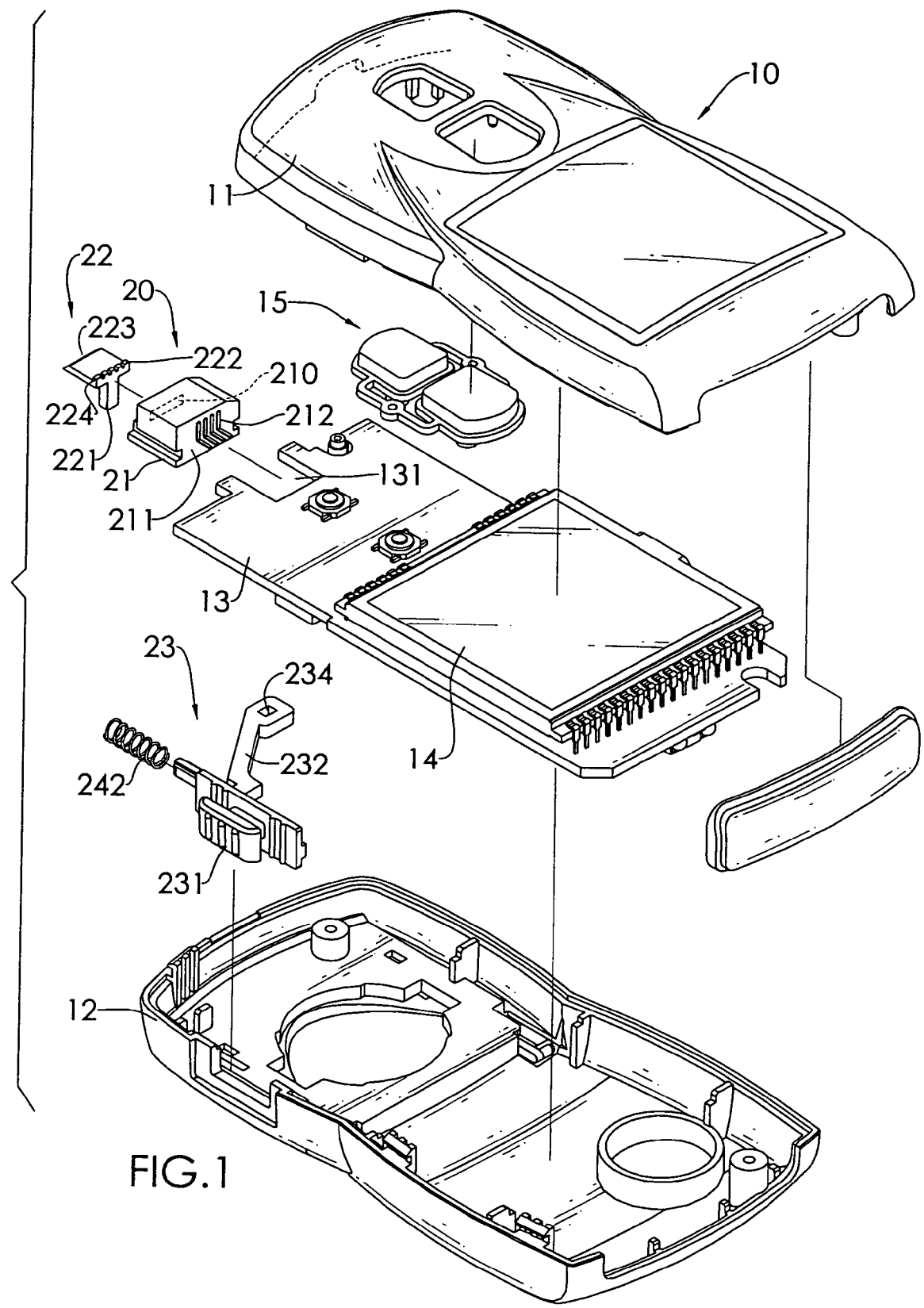
FIG. 1 is an exploded perspective view of the reader of the present invention.

With reference to FIG. 1, it is noted that a bio reader in accordance with the present invention includes a hollow casing (10) composed of a top cover (11) and a bottom cover correlated with the top cover (11) to define therebetween a receiving space, a strip connector (20) firmly engaged with a peripheral edge of both the top cover (11) and the bottom cover (12) and a retracting finger (23) movably received in the casing (10) to drive a push (22) movably received in the strip connector (20).

Further, the casing (10) has a circuit board (13) electrically sandwiched between the strip connector (20), a monitor (14) connected to the circuit board (13) to display readings from the strip (not shown) and control buttons (15) mounted on top of the circuit board (13) and exposed from the top cover (11) for control of functions of the bio reader of the present invention. In order to mate the strip connector (20), the circuit board (13) has a cutout (131) defined in a peripheral edge thereof so that the strip connector (20) is able to be received in the cutout (131).

The strip connector (20) further has a hollow base (21) mounted in the casing (10), an inlet (210) defined in a side face of the base (21) to receive a strip (not shown in this drawing) therein, a sliding space (211) defined in a bottom face of the base (21), multiple contact legs (212) firmly received inside the base (21) and extending out to connect to the circuit board (13) and the push (22) movably connected inside the base (21) and having an extension (221) extending downwards, out of the sliding space (211) of the base (21), a ridge (222) formed on a top face of the push (22) and recesses (224) defined in the ridge (222).

The retracting finger (23) is slidably sandwiched between the top cover (11) and the bottom cover (12) and includes a slidable button (231), a linkage (232) extending from a side of the slidable button (231), a hole (234) defined in a free end of the linkage (232) and a guiding rod extending from the retracting finger (23) and is mounted to a compression spring (24).

Figure 2:
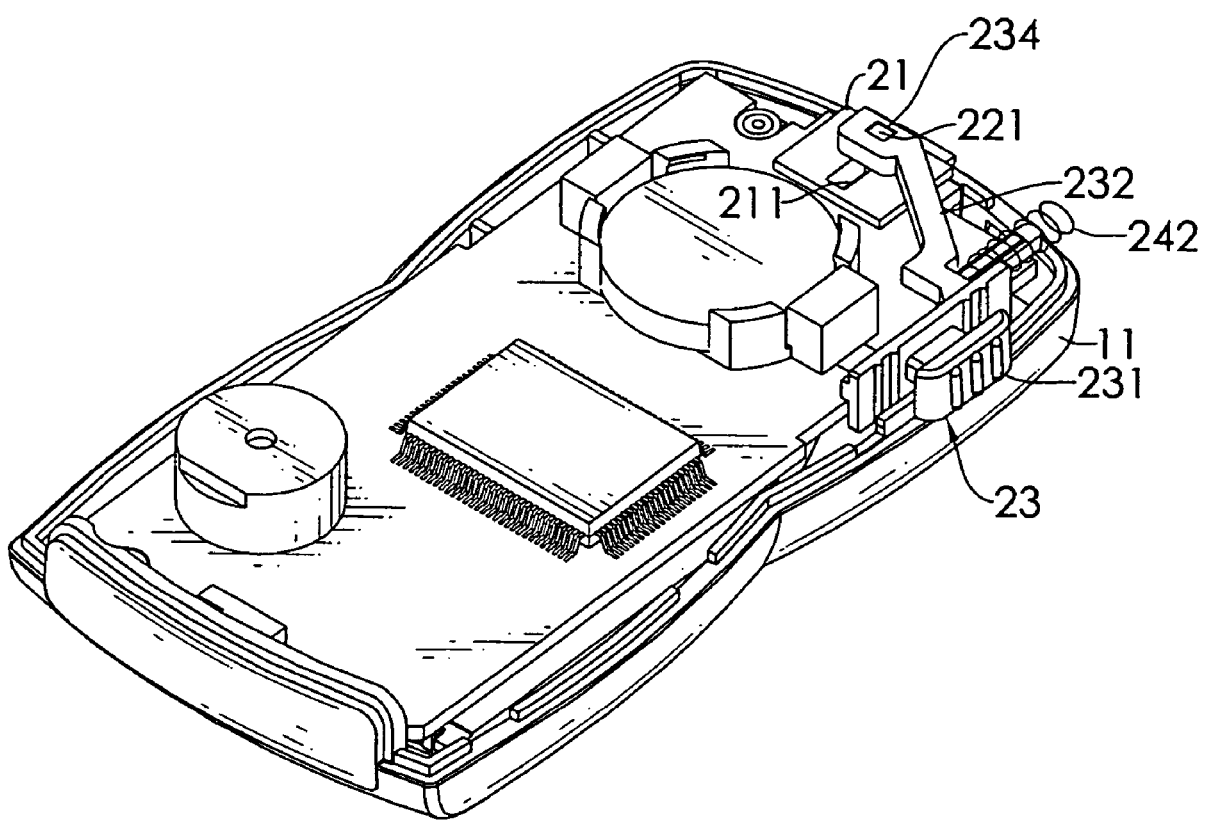
FIG. 2 is a perspective view showing the assembled reader with the bottom cover removed.
Figure 3:
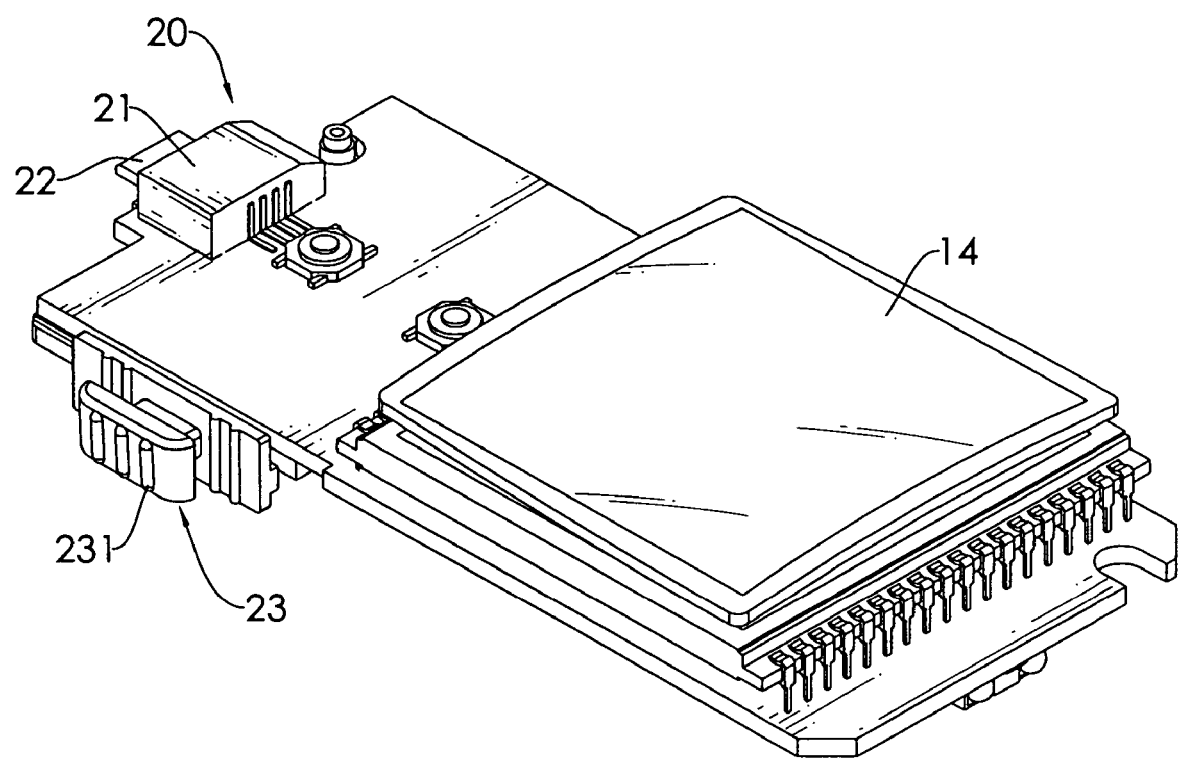
FIG. 3 is a perspective view showing the assembled reader with the top cover and the bottom cover removed.
Figure 4A:
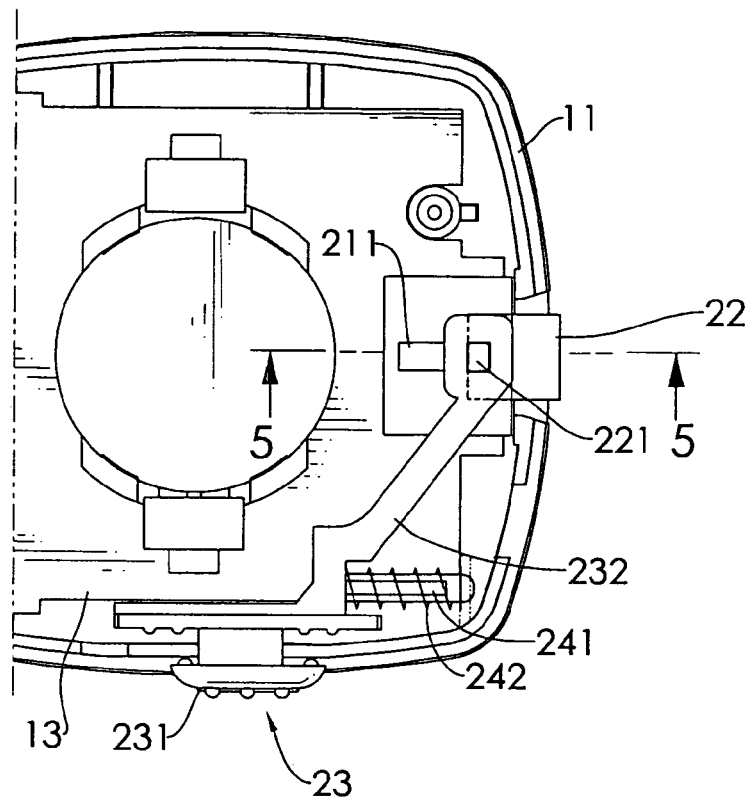
FIG. 4A is a schematic top plan view showing partial structural relationship inside the reader.
Figure 4B:
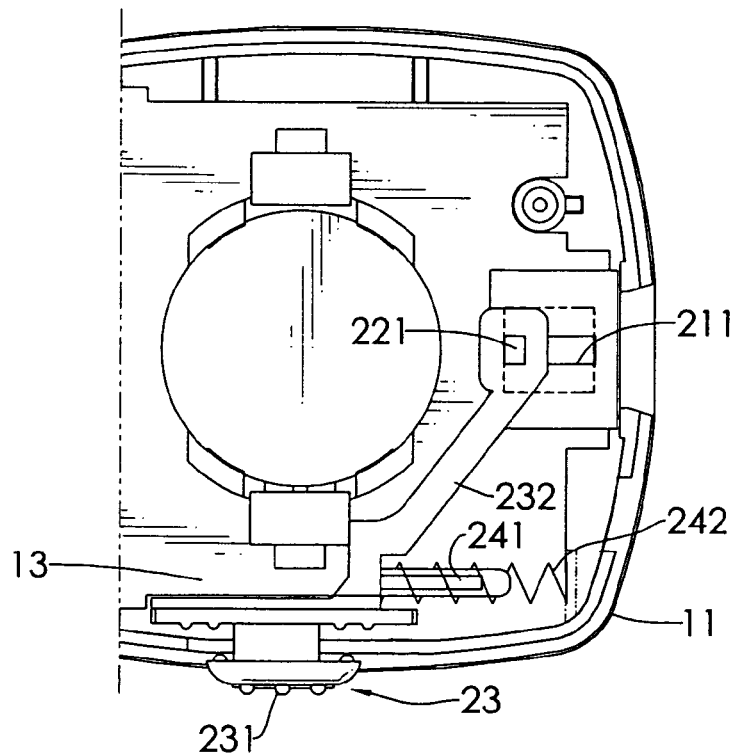
FIG. 4B is a schematic top plan view showing partial structural relationship inside the reader after the slidable button is moved by the recoil spring to its original position.

With reference to FIGS. 2 and 3 and still using FIG. 1 for reference, when the bio reader of the present invention is assembled, the circuit board (13) and the monitor (14) are firmly received between the top cover (11) and the bottom cover (12). The strip connector (20) is securely received in the cutout (131) to have the contact legs (212) electrically connected to the circuit board (13) and the control buttons (15) are electrically mounted on the circuit board (13) and extended out of the top cover (11) so that an operator is able to use the control buttons (15) to command the circuit board (13) to proceed functions as required.

With reference to FIGS. 4A, 4B, 5 and 6, it is noted that the push (22) is received in the strip connector (20) with the extension (221) extending out of the sliding space (211) such that a portion of the contact legs (212) received inside the strip connector (22) is in contact with a top face of the push (22). Then a free end of the extension (221) is extended into the hole (234) of the linkage (232) of the retracting finger (23). Finally the compression spring (242) is mounted around the guiding rod and abutted by a body of the retracting finger (23) and an inner side of the casing (10).

Therefore, it is seen that when the slidable button (231) is moved, due to the linkage (232) being securely connected to the extension (221) of the push (22), the push (22) is also moved.

Figure 5:
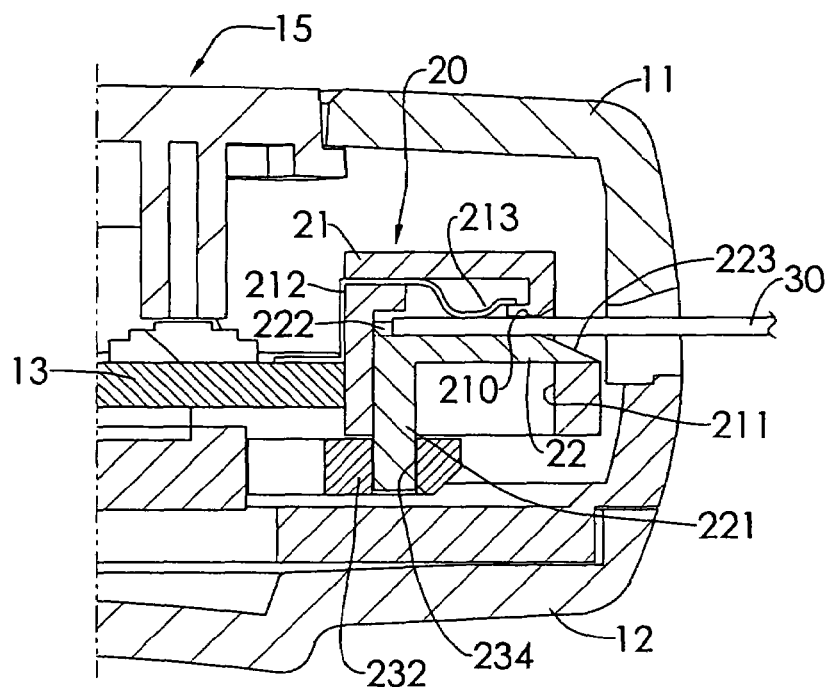
FIG. 5 is a schematic cross sectional view taken from line 5-5 in FIG. 4A.
Figure 6:
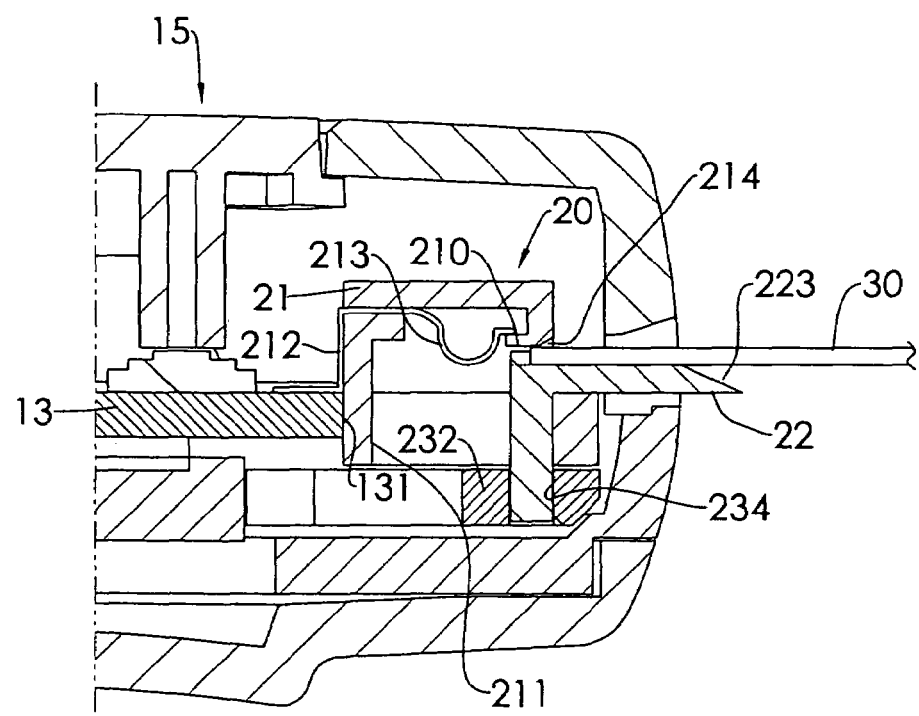
FIG. 6 is a schematic cross sectional view showing that the strip is easily removed from the reader.

As shown in FIGS. 5 and 6, after a strip (30) is inserted into the bio reader of the present invention from the inlet (210) and abutted by the ridge (222) of the push (22), arcuate portions (213) of the contact legs (212) are in contact with the strip (30) so that bio information contained on the strip (30) is read by the bio reader of the present invention. After the bio information is read, the operator is able to move the slidable button (231) toward the inlet (210) to allow the push (22) to be simultaneously moved toward the inlet (210). In the meantime, the recesses (224) in the ridge (222) move respectively through the arcuate portions (213) of the contact legs (212) so that the arcuate portions (213) of the contact legs (212) will not hinder movement of the push (22). It is noted that when the push (22) is moved, the strip (30) on top of the push (22) is also moved. When the slidable button (231) is moved toward the inlet (210), the compression spring (242) is compressed such that after the operator releases the slidable button (231), the recoil force from the compression spring (242) pushes the retracting finger (23) as well as the push (22) back to their original positions to be ready for the next process.

In order to facilitate the extension of the strip (30) into the bio reader of the present invention, an oblique face (214) is formed on a peripheral face defining the inlet (210) and the push (22) also has an inclined face (223).

As a conclusion, the retracting process of the strip (30) is entirely hand-free so that either the medical specialist or the bio sample on top of the strip is not affected and potential dangers of infection or contamination are avoided.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A bio reader comprising a hollow casing receiving therein a circuit board, a monitor and a strip connector; wherein:
   the strip connector is adapted to receive therein a strip and has
      a base being hollow and mounted in the casing;
      a push movably connected inside the base of the strip connector and having a ridge formed thereon and adapted for abutment of a strip on top of the push and an extension extending out of the base; and
      a retracting finger securely connected to the extension of the push and slidably mounted on a side of the casing such that movement of the retracting finger is able to drive the extension of the push to move such that the strip on top of the push is also moved; and
      the circuit board is connected electrically to the monitor and the strip connector.

2. The bio reader as claimed in claim 1, wherein the retracting finger has a linkage extending from the retracting finger and having a hole defined in a free end of the linkage to correspond to and receive therein a free end of the extension of the push such that the movement of the retracting finger is able to drive the push to move.

3. The bio reader as claimed in claim 1, wherein the strip connector has a sliding space defined in a bottom face of the base and the extension of the push is able to extend out of the sliding space.

4. The bio reader as claimed in claim 2, wherein the strip connector has a sliding space defined in a bottom face of the base and the extension of the push is able to extend out of the sliding space to connect to the linkage so that the movement of the retracting finger drives push to move.

5. The bio reader as claimed in claims 1-4, wherein the strip connector has contact legs composed of a portion extending out of the base for electrical connection with the circuit board and a portion received inside the base for engagement with the strip and having an arcuate portion.

6. The bio reader as claimed in claim 5, wherein the push has recesses defined in the ridge to facilitate the movement of the push in relation to the contact legs.

7. The bio reader as claimed in claim 6 further comprising a compression spring adapted to be abutted between an inner side of the casing and the retracting finger so that recoil force from the compression spring due to the movement of the retracting finger is able to return the retracting finger to its original position.

8. The bio reader as claimed in claim 7, wherein the retracting finger further has a guiding rod extending therefrom and the compression spring is mounted around the guiding rod.

9. The bio reader as claimed in claim 8, wherein an oblique face is formed on a peripheral face defining an inlet defined in the base of the strip connector and an inclined face is formed on the push so that the extension of the strip into the bio reader is facilitated.

\* \* \* \* \*